United States Patent [19]
Greier et al.

[11] Patent Number: 5,352,692
[45] Date of Patent: Oct. 4, 1994

[54] THIOPHENE-2-CARBOXYLIC ACID DERIVATIVES

[75] Inventors: Gerhard Greier, Linz; Dieter Binder, Vienna, both of Austria

[73] Assignee: Laevosan Gesellschaft M. B. H., Linz, Austria

[21] Appl. No.: 938,166
[22] PCT Filed: Apr. 1, 1992
[86] PCT No.: PCT/AT92/00044
§ 371 Date: Feb. 4, 1993
§ 102(e) Date: Feb. 4, 1993
[87] PCT Pub. No.: WO92/17472
PCT Pub. Date: Oct. 15, 1992

[30] Foreign Application Priority Data
Apr. 4, 1991 [AT] Austria ................... 716/91

[51] Int. Cl.$^5$ ............... A61K 31/415; C07D 409/12
[52] U.S. Cl. ................... 514/397; 548/315.1
[58] Field of Search .......... 548/315.1; 514/397

[56] References Cited
U.S. PATENT DOCUMENTS
3,795,681 3/1974 Ruschig et al. ........... 548/315.1

FOREIGN PATENT DOCUMENTS
0109381 5/1984 European Pat. Off. .
2126597 12/1972 Fed. Rep. of Germany .
2065121 6/1981 United Kingdom .

OTHER PUBLICATIONS
*Chemical Abstracts*, vol. 103, 1985, 103:134809z.
*Chemical Abstracts*, vol. 104. 1986, 104: 14751y.
*Chemical Abstracts*, vol. 113, 1990, 113: 97353e.

*Primary Examiner*—Patricia L. Morris
*Attorney, Agent, or Firm*—Sughrue, Mion, Zinn, Macpeak & Seas

[57] ABSTRACT

There are described novel compounds of the general formula

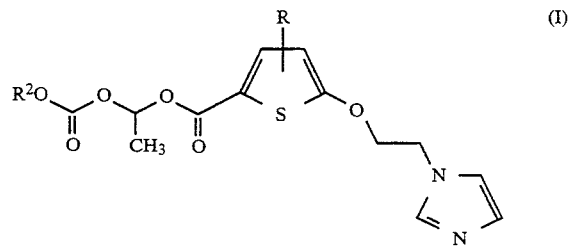

in which R in position 3 or 4 is hydrogen, methyl, chlorine or bromine and $R^2$ is $C_1$–$C_{10}$-alkyl, $C_3$–$C_7$-cycloalkyl or benzyl, and the pharmaceutically acceptable addition salts thereof with weak organic acids as well as a process for the preparation thereof.

The compounds of formula (I) are inhibitors of thromboxane synthetase.

5 Claims, No Drawings

THIOPHENE-2-CARBOXYLIC ACID DERIVATIVES

The invention relates to novel therapeutically valuable derivatives of thiophene-2-carboxylic acid and to a process for the preparation thereof.

EP-A1-0 109 381 discloses a compound of formula (I')

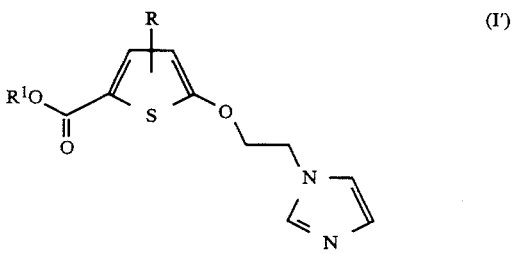

in which R in position 3 or 4 is hydrogen, methyl, chlorine or bromine and $R^1$ is hydrogen or $C_1$–$C_4$-alkyl, having a potent inhibitory effect on thromboxane synthethase without a significant inhibition of the effect of the enzymes prostacycline synthetase or cyclooxygenase from microsomes of thrombocytes.

However, when orally administered, the compound of formula (I'), in which $R^1$ is H, has only a low resorption.

Now it has been found that the 1-alkoxycarbonyloxyethyl esters of the compound of formula (I') have an improved resorption, when orally administered, since after passage through the intestinal tract they are present in the blood in form of the free carboxylic acid. Therefore, they are suitable prodrugs of the compound of formula (I').

Thereby, the compounds of the invention having the formula (I) given below have, when orally administered, a strong inhibitory effect on the thromboxane synthetase without a significant inhibition of the effect of the enzymes prostacycline synthetase or cyclooxygenase from microsomes of thrombocytes, i.e. these compounds inhibit the conversion of prostaglandin-$H_2$ into thromboxane $B_2$ via thromboxane $A_2$, being an unstable intermediate product, from which it is known that it induces the irreversible aggregation of platelets and contracts smooth muscles, especially those of the blood vessels. This fact shows that the compounds of formula (I) inhibit the biosynthesis of thromboxane $A_2$ and thus are suitable for the treatment of diseases caused by thromboxane $A_2$ such as inflammatory disease, hypertension, thrombus, apoplexy, asthma, angina pectoris, ischemic heart disease, ischemic attacks, migraine and vascular complications of diabetes.

Thus, subject matter of the present invention are novel compounds of the general formula (I)

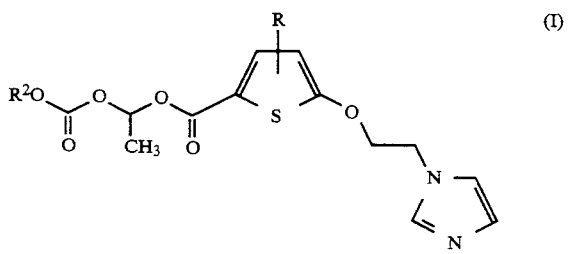

in which R in position 3 or 4 is hydrogen, methyl, chlorine or bromine and $R^2$ is $C_1$–$C_{10}$-alkyl, $C_3$–$C_7$-cycloalkyl or benzyl, and the pharmaceutically acceptable addition salts thereof with weak organic acids.

The resorption of the compounds of the invention, when orally administered, is at least three times the degree of the resorption of the compounds of EP-A1-0 109 381, when orally administered.

A further subject matter of the present invention is a process for preparing the novel compounds of formula (I), in which R and $R^2$ are as defined above, comprising the reaction of a salt of a compound of formula (I'')

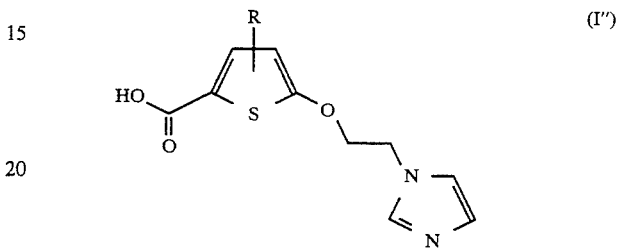

in which R is as defined above, with a compound of the general formula (II)

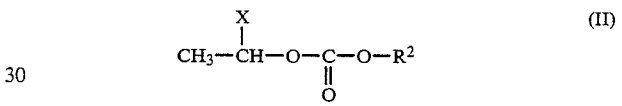

in which X is a leaving group suitable for nucleophilic replacement, such as e.g. halogen, preferably chlorine or bromine, and $R^2$ is as defined above, and the conversion of the obtained compound of formula (I) into an addition salt with a weak organic acid.

The reaction is carried out usually by addition of at least one equivalent of a strong base, such as e.g. an alkali hydride or alkali carbonate, to a solution of the starting compound in an anhydrous inert organic aprotic solvent, such as e.g. hexamethylphosphoric acid triamide, dimethylformamide or dimethylsulfoxide, and addition of the compound of formula (II), preferably in equivalent amounts or in a slight excess in the same solvent.

The reaction is carried out at a temperature in the range of room temperature to about 100° C. Generally it is preferred to heat the reaction mixture, e.g. to 80° C., so as to accelerate the reaction. Under these conditions the reaction is completed usually within 2.5 hours.

The reaction mixture is worked up in conventional manner, for instance by solvent extraction.

The compounds of formula (I) of the invention having a basic imidazole group can be converted into their pharmaceutically acceptable salts with weak organic acids in usual manner. Examples of suitable acids are fumaric, oxalic, malonic, succinic, adipic, maleinic, tartaric or citric acid.

The preparation of the starting compound is described in EP-A1-109 381.

The present invention relates also to the use of the novel compounds of formula (I) alone or in mixture with other active substances in form of usual oral galenic compositions. The compounds of the invention can be administered orally in the form of tablets or capsules containing an unit dosage of the compound together with diluents, such as corn starch, calcium carbonate, dicalcium phosphate, alginic acid, lactose, magnesium stearate, primogel or talcum. The tablets are prepared in usual manner by granulating the ingredients and compressing and the capsules are prepared by filling into hard gelatine capsules of suitable size.

It is supposed that for the oral administration to humans the daily dosage amount of a compound of the invention is in the range of 0.1 to 20 mg/kg per day for a typical adult patient weighing 70 kg. Therefore, tablets or capsules may contain usually 5 to 150 mg of the active compound for the oral administration up to three times per day.

Of course, in each case the physician will determine the actual dosage most suitable for the individual patient, which dosage may vary depending on the age, the weight and the response of the patient.

The following example should illustrate the invention, however, without limiting it thereto.

EXAMPLE 1

To a solution of 5 g (18.20 mmoles) of the hydrochloride of 5-2-( 1H-imidazole-1-yl )-ethoxy]-thiophene-2-carboxylic acid in 100 ml of hexamethylphosphoric acid triamide (HMPT) 2 g of NaH (80% suspension) are added in portions with good stirring at room temperature. Thereby the temperature increases to about 40° C. For formation of a salt it is stirred for 1 hour at room temperature and then a solution of 4.2 g (27.52 mmoles) of 1-chloroethylethylcarbonate in 6 ml of HMPT is dropped in at room temperature.

The reaction mixture is heated for 2.5 hours to 80° C. and then partitioned between ice-water and ethylacetate (EtOAc). The phases are separated, the aqueous phase is extracted three times with EtOAc and the organic phase is extracted twice with a saturated solution of NaHCO$_3$. The EtOAc-phase is extracted three times with 2N HCl. The HCl-Phase is neutralized with ice cooling and then extracted exhaustively with EtOAc.

After drying over Na$_2$SO$_4$ it is filtered and evaporated. There are obtained 5.78 g of a yellow oil, which is purified by column chromatography: silica gel, CH$_2$Cl$_2$/ethanol=20:1. There are obtained 4.43 g of the ethoxycarbonyloxyethyl ester of 5-[2-(1H-imidazole-1-yl)-ethoxy]-thiophene-2-carboxylic acid as pale yellow oil (68.7% of theory).

For forming the fumarate the oil is dissolved in a small amount of ethanol p.A. and the equimolar amount of fumaric acid (dissolved in ethanol/methanol=6:1) is added at −8° C. After stirring for several hours with ice-water cooling it is evaporated carefully and the residue is caused to crystallize with icecold ether. The obtained fumarate is recrystallized from EtOAc giving 4.0 g of the 1-ethoxycarbonyloxyethyl ester fumarate of 5-[2-(1H-imidazole-1-yl )-ethoxy]-thiophene-2-carboxylic acid (62% of theory), m.p. 73°-75° C., in form of colorless crystals. TLC: CH$_2$Cl$_2$/ethanol=12: 1.

Elementary microanalysis: Calculated for C$_{19}$H$_{22}$N$_2$O$_{12}$S: C 48.51; H 4.71; N 5.95%; found: C 48.49; H 4.59; N 5.97%. MW=470.46 $^1$H-NMR (DMSO): 7.50 (s, 1H, Im-H$_2$); 7.36; 7.31; 6.11; 6.06 (AB, 2H, Th-H$_3$ and Th-H$_4$); 6.87 (s, broad, 2H, Im-H$_4$ and Im-H$_5$); 6.68 (q, 1H, —CH—CH$_3$); 6.55 (s, 2H, —CH=CH—); 4.18 (h, 4H, —OCH$_2$CH$_2$—); 3.98 (q, 2H, —OCH$_2$—CH$_3$); 1.37 (d, 3H, CH$_3$—CH—); 1.08 (t, 3H, —OCH$_2$—CH$_3$).

We claim:

1. A compound of formula (I)

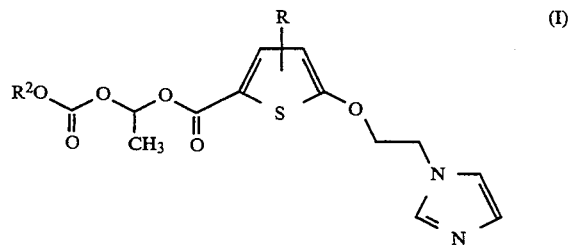

in which R in position 3 or 4 is hydrogen, methyl, chlorine or bromine and R$^2$ is C$_1$-C$_{10}$-alkyl, C$_3$-C$_7$- cycloalkyl or benzyl, or a pharmaceutically acceptable addition salt thereof with weak organic acids.

2. 1-Ethoxycarbonyloxyethyl ester of 5-[2-(1H-imidazole-1-yl)-ethoxyl]-thiophene-2-carboxylic acid.

3. 1-Ethoxycarbonyloxyethyl ester fumarate of 5-[2-(1H-imidazole-1-yl)-ethoxy]-thiophene-2-carboxyl acid.

4. Pharmaceutical composition for oral administration, characterized in that it comprises an effective amount compound of formula (I) as defined in claim 1, or a pharmaceutically acceptable addition salt thereof with a weak organic acid, together with a pharmaceutically acceptable carrier or diluent.

5. A method of use of a compound of formula (I) as defined in claim 1, comprising administering a compound of formula (I) in the form of a medicament in an amount thereof effective as an inhibitor of thromboxane synthetase for treating diseases caused by thromboxane A$_2$.

* * * * *